United States Patent [19]
van Krieken

[11] Patent Number: 5,674,254
[45] Date of Patent: Oct. 7, 1997

[54] CARDIAC PACEMAKER SYSTEM AND METHOD FOR DETERMINING A MEASURE OF PACING THRESHOLD WITHOUT INCURRING LOSS OF CAPTURE

[75] Inventor: Frits M. van Krieken, Dieren, Netherlands

[73] Assignee: Vitatron Medical, B.V., Dieren, Netherlands

[21] Appl. No.: 445,667

[22] Filed: May 22, 1995

[51] Int. Cl.$^6$ .................................................. A61N 1/365
[52] U.S. Cl. .................................................. 607/11; 607/28
[58] Field of Search .................................. 607/28, 11, 9

[56] References Cited

U.S. PATENT DOCUMENTS

| | | | |
|---|---|---|---|
| 5,391,192 | 2/1995 | Lu et al. | 607/28 |
| 5,411,533 | 5/1995 | Dubreuil et al. | 607/28 |
| 5,417,718 | 5/1995 | Kleks et al. | 607/28 |
| 5,476,487 | 12/1995 | Sholder | 607/28 |

Primary Examiner—William E. Kamm
Assistant Examiner—Kennedy J. Schaetzle
Attorney, Agent, or Firm—Woodcock Washburn Kurtz Mackiewicz & Norris LLP

[57] ABSTRACT

A implantable cardiac pacemaker system which is battery powered, having an improved capability for monitoring patient threshold and adjusting pace pulse output to an optimized safety factor above patient threshold, thereby avoiding excessive energy expenditure in delivery of pace pulses and maximizing pacemaker lifetime. The improved threshold tracking system analyzes information from detected heart signals and correlates changes in such heart signal information to pulse output energy, enabling a determination of when the pulse output energy is near threshold without dropping below threshold. In a preferred embodiment, changes in the QT interval are monitored and correlated with changes in output pulse energy, enabling the pacemaker to obtain a measure of patient threshold without dropping pulse energy below threshold and suffering loss of capture.

17 Claims, 5 Drawing Sheets

CARDIAC PACEMAKER SYSTEM AND METHOD FOR DETERMINING A MEASURE OF PACING THRESHOLD WITHOUT INCURRING LOSS OF CAPTURE

BACKGROUND OF THE INVENTION

This invention relates to pacemaker systems and methods for delivering pace pulses to a patient's heart and, in particular, a pacemaker system having a capability for determining a measure of the patient's pacing threshold.

There are presently a wide variety of different types of pacemakers available for treating differing patient cardiac conditions. Pacemakers may be single chamber or dual chamber types, they may be rate controlled, and may be programmable to perform any number of different functions. Such modern implantable cardiac pacemakers are powered by batteries, typically lithium iodide batteries. These batteries have capacities varying typically from 600 mAh up to 1800 mAh, the choice of battery capacity depending upon the complexity of the pacemaker and the different functions to be performed. These batteries lead to pacemaker lifetimes typically in the range of about 5–8 years. Of course, the actual lifetime of the pacemaker will depend upon operating conditions, i.e., the ongoing current drain due to delivery of pace pulses and the continuous operation of the pacemaker circuitry for carrying out programmed functions.

Whatever the particular pacemaker model and battery capacity, it is desirable to minimize current drain, and thus maximize effective pacemaker lifetime. Most of the pacemaker operations are fixed in the sense that they cannot be programmed on or off, such that there is a base level of current drain and consequent battery expenditure. However, the output level of the delivered pace pulses, i.e., the energy in each delivered pace pulse, is a variable that can be programmed in most pacemakers, either by external programming or an automatic internal adjustment. The energy content of the pace pulse can be varied either by adjustment of the voltage, or the pulse width, or both. It is well known that adjustment of the delivered pace pulses to the lowest safe level to provide effective pacing can have a significant effect in maximizing the pacemaker lifetime.

In order to maintain safe pacing at an effective minimal level, it is known that there must be a determination of the patient pacing threshold, the pace pulse energy level at which a delivered pulse actually causes contraction of the heart, or what is termed "capture." The patient threshold can be determined by dropping the energy level of delivered pace pulses to a point where a delivered pulse no longer captures the heart, and determining the energy level with which capture is lost. Typically at time of implant of a pacemaker threshold is determined by changing the output level and monitoring the response with external electrodes and leads. However, it is also known that threshold changes after implant can be subject to significant variations thereafter during the lifetime of the pacemaker. For this reason, there have been for some time systems developed for automatic detection of threshold. See, for example, the early patent to Bowers, U.S. Pat. No. 3,835,865. This patent illustrates automatic decrementing of the pulse output until loss of capture, at which point threshold is determined and the output level is reprogrammed to a safe level above threshold.

There have been a number of other pacemaker designs for detecting threshold. See, for example, U.S. Pat. No. 5,176,138, which provides a means for automatically adjusting the energy of the stimulation pulse as a function of the amount of $SO_2$ sensed in the blood of the pacemaker patient. This technique is based on the observation that there is a detectable change in the $SO_2$ level when there is no capture. The pacemaker using this technique is programmed to drop the pulse level below threshold so as to determine the $SO_2$ level which corresponds to when the patient is no longer being paced.

To date, all threshold tracking arrangements have been based upon a technique of determining when the output level has dropped below threshold, such that there is failure of capture. Consequently, pacemakers incorporating such techniques require that the patient go through a sequence where pacing is caused to fail, in order to make a determination of threshold. The use of backup pulses to minimize the effective loss of capture is disclosed in the above-referenced Bowers patent. However, backup pulses require extra energy, as well as additional circuitry.

As a consequence, there remains a need for accurately tracking threshold with a procedure that does not require loss of capture. Effective threshold tracking enables adjustment of the stimulation energy to be set at a safe level above threshold, thereby avoiding a higher energy setting which excessively depletes the limited energy available from the pacemaker battery. Such a threshold technique is preferably one which can be repeated on a regular basis without causing discomfort to the patient, because threshold may change significantly for any given patient over time and in response to differing physiological conditions. What is needed in the art is an effective means for automatically obtaining a measure of threshold without loss of pacing.

SUMMARY OF THE INVENTION

The present invention meets the objective of a pacemaker having a capability to automatically determine a measure of patient pacing threshold without causing the patient to undergo loss of one or more heartbeats. The invention provides a pacemaker that can monitor variations in the patient's cardiac signal caused by variations in output power level, such that a measure of threshold can be estimated, or extrapolated without loss of capture, based upon changes in the monitored cardiac signal that correspond to changes in pace pulse output level.

Specifically, in accordance with one preferred embodiment of the present invention, the pacemaker is provided with a capability of changing the pace pulse output level and determining corresponding changes in the QT interval, i.e., the time interval between a delivered stimulus or the QRS wave evoked thereby, and the resulting T-wave. The pacemaker takes measurements of the QT interval at a series of decreasing values of output level, and based upon stored data correlating QT with output level, determines when output level is just above threshold, thereby providing a measure of threshold without undergoing loss of capture. The preferred QT embodiment is based upon measurements showing a lengthening of QT interval corresponding to decreased pace pulse output. It is considered that a likely reason for this variation is that as the energy level of the delivered pace pulses approach threshold, fewer cells around the pacing electrode are stimulated. As a consequence, further propagation of the depolarization front takes increasing time, and also slows down the repolarization, thus lengthening the associated QT interval. For the same reasons, there is a change in the morphology of the evoked QRS wave, as well as the morphology of the T-wave, i.e., a change in the time or frequency profile of each of these waves. Thus, information relating pulse output energy level to the threshold can be obtained by examining different features of the patient cardiac signal. Thus, while correlation of QT interval to pace pulse output is illustrated as a preferred embodiment, the invention applies generally to correlating sensed cardiac signals following delivery of pace pulses to the output levels of the delivered pace pulses.

DESCRIPTION OF THE PREFERRED EMBODIMENTS

Figure 1:
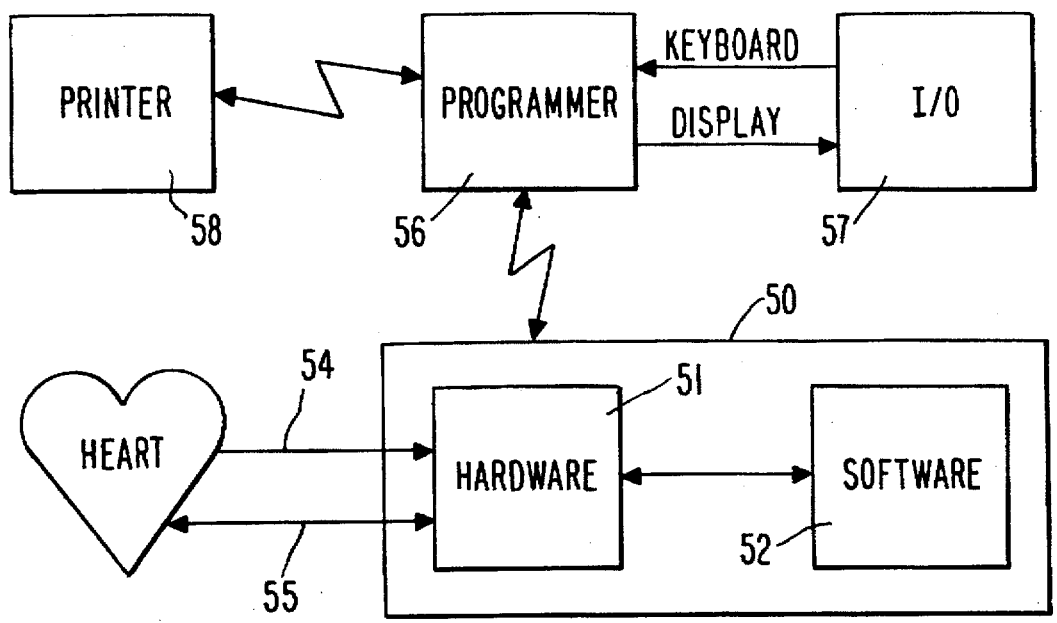
FIG. 1 is a system diagram showing the pacemaker system of this invention in relation to the patient's heart and to external programmer and data entry and display apparatus.

The pacing system of this invention is preferably software-based, i.e., the software controls functions through hardware, as illustrated in FIG. 1. Referring specifically to FIG. 1, the pacemaker 50 is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes on lead 55, and one or more sensor connections 54. As is well understood in the art, for a dual chamber pacemaker, there are generally two leads, an atrial lead and a ventricular lead, each lead having at least one electrode, unipole or bipole, positioned in the heart. For a VDD pacing system, there is only one lead, but there are still separate A and V electrodes. Line 54 is illustrated as leading to the heart, as with the QT-type sensor arrangement of the preferred embodiment. Additional sensors may be attached to the outside case of the pacemaker or may couple to any other available sensors for sensing body parameter information used in rate responsive pacing systems. Further, in the preferred embodiment of the pacing system of this invention, sensor link 54 may comprise a pair of sensors, e.g., QT plus activity, as set forth in U.S. Pat. No. 5,065,759.

As further illustrated in FIG. 1, the pacer 50 is in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 2:
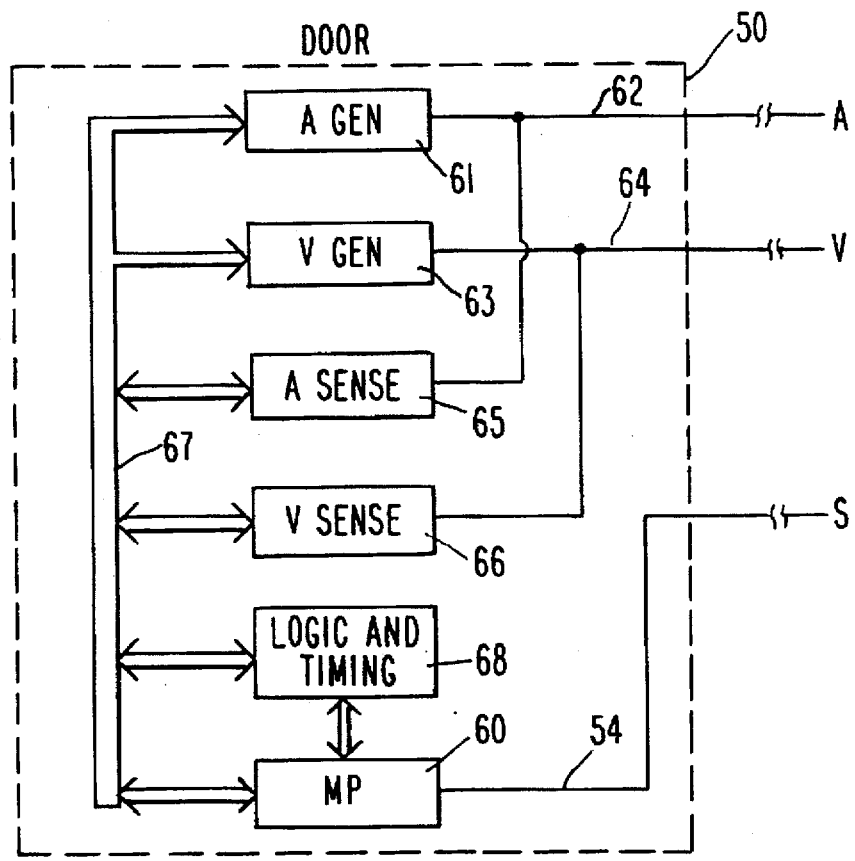
FIG. 2 is a block diagram which illustrates basic components of the pacemaker of this invention, together with leads and a sensor for delivering signals to and/or receiving signals from the patient.

Referring to FIG. 2, there is shown a basic block diagram of primary hardware components of an illustrative DDDR pacer 50. An atrial generator 61 is shown, having an output connected to lead 62 which communicates with the patient's atrium. An A-sense amplifier 65 is illustrated also connected to atrial lead 62. A ventricular generator is illustrated which is connected to the patient's ventricle through lead 64. V-sense amplifier 66 is also connected to lead 64, to receive and sense signals from the patient's ventricle. V-sense block 66 also includes means for picking out and determining the timing of the evoked T-wave. See U.S. Pat. Nos. 4,305,396 and 4,665,919, incorporated herein by reference, which illustrate T-wave sensing and QT determination. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. As affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function is well known in the art, such that the following detailed discussions of software routines enable one of ordinary skill in this art area to design a system for carrying out the functions within the scope of the invention. Data inputted from programmer 56 is stored in memory associated with microprocessor 60.

Still referring to FIG. 2, there is shown a sensor S indicated as providing an input to microprocessor system 60. Sensor S represents one or more sensors for monitoring one or more body parameters to provide an indication of desired pacing rate. The pacemaker of this invention may be rate responsive in the manner as described in the referenced U.S. Pat. No. 5,247,929.

Figure 3A:
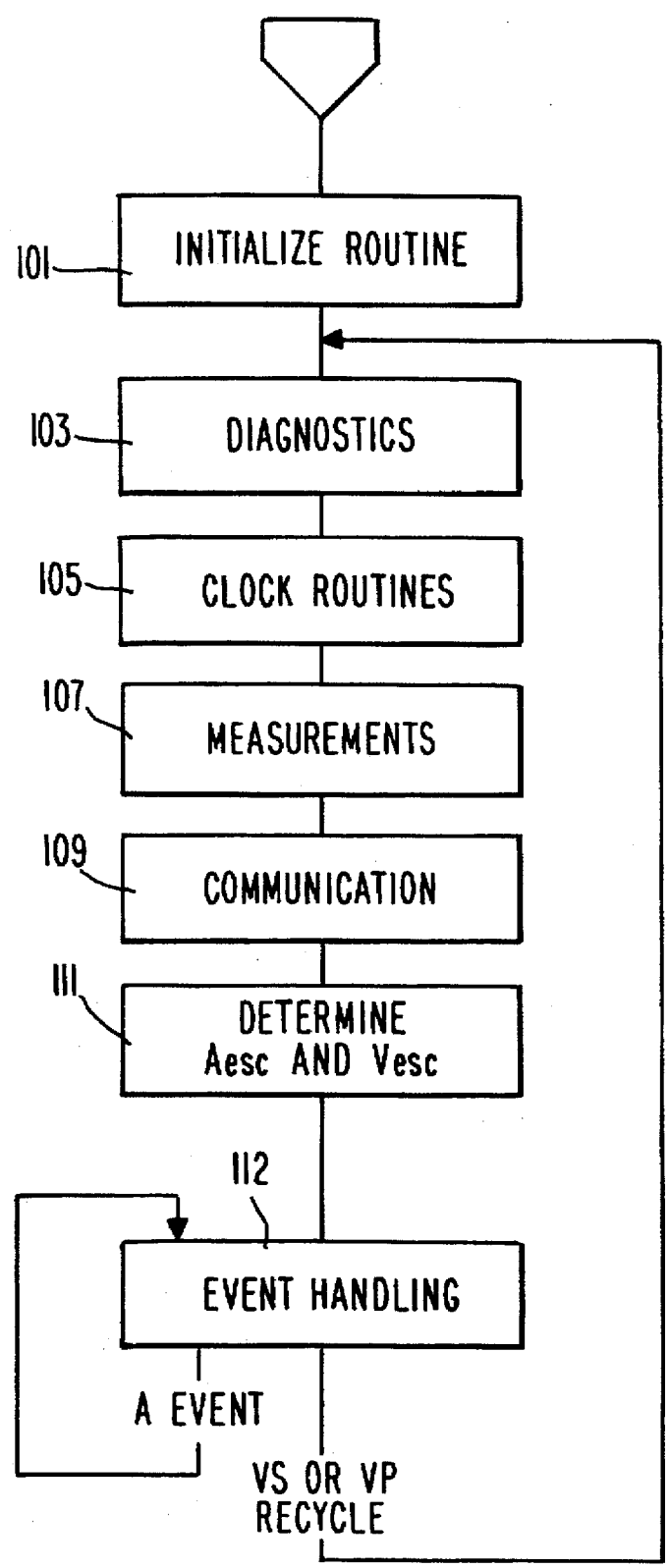
FIG. 3A is a flow diagram carried out cyclically, showing the primary operation and overall logic structure of the pacemaker of this invention.

Referring now to FIG. 3A, there is shown an illustrative flow diagram of the basic operational and logical steps performed by the pacemaker of this invention. The routine is initialized at 101. Following this, any diagnostics spilled into the pacer are performed at block 103, and clock routines are done at block 105. Measurements are performed and measure data stored at 107. Thus, determinations of QT interval and/or measurements of the characteristics of the QRS or T-wave are performed as part of this operation. Any communications with an external device such as programmer 56 are done at step 109. The routine then goes to step 111, and determines A_esc and V_esc for the coming cycle. Of course, for a single chamber device only a single escape interval is determined. Following this, the pacemaker carries out event handling at 112, e.g., for a dual chambered pacemaker it reacts to atrial and/or ventricular senses, and delivers pace pulses as required by timeout of escape intervals. Following the ventricular event, either VS or VP, the pacemaker returns for the next operational cycle.

Figure 3B:
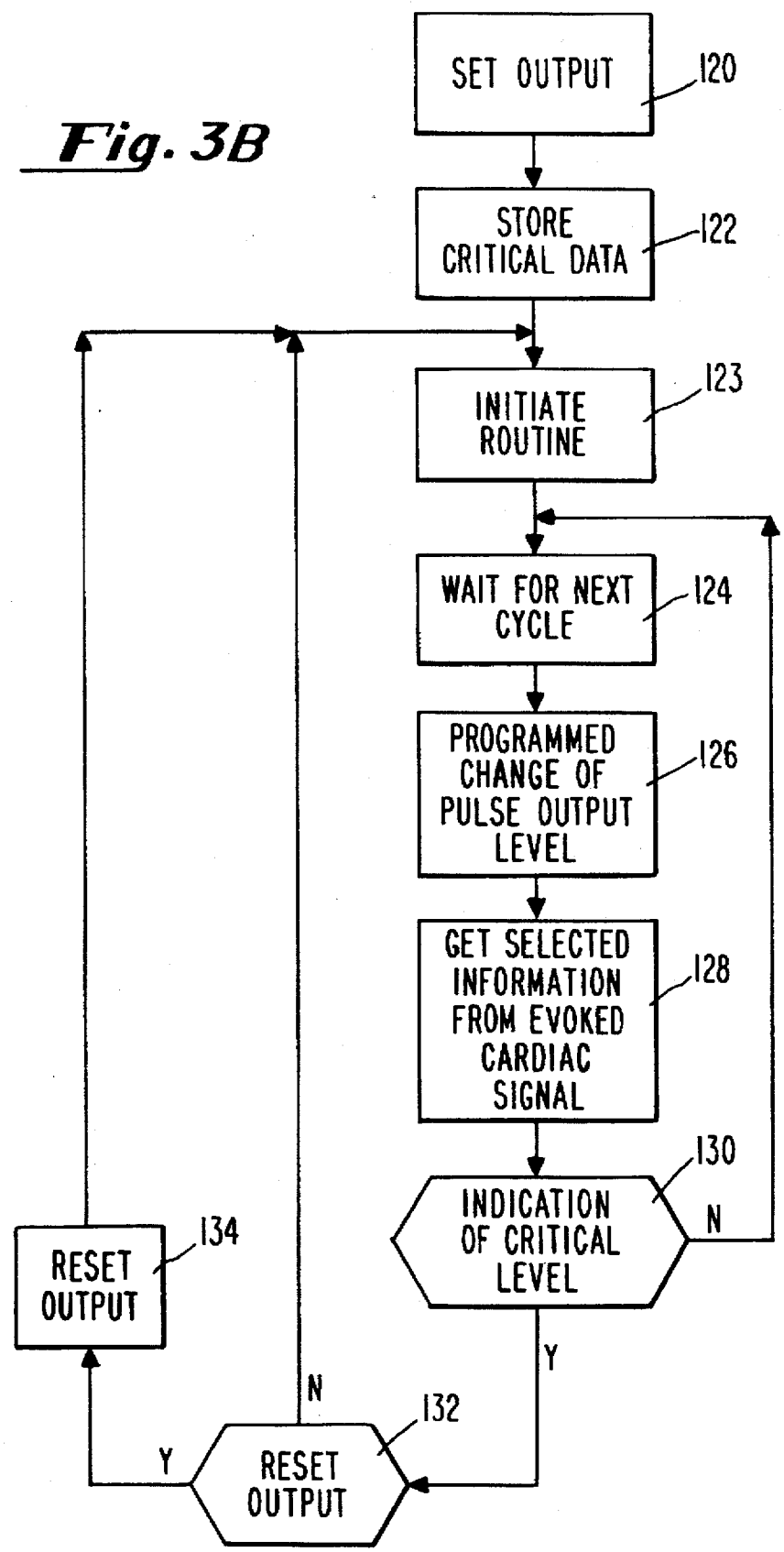
FIG. 3B is a flow diagram of a general routine for obtaining a measure of patient threshold without loss of capture.

Referring to FIG. 3B, there is shown a simplified flow diagram of the primary steps taken in practicing the method of this invention. At block 120, the output level of pace pulses is set. This may be done initially by the physician at the time of implant, or may be done later either by external programming or automatically. At block 122, critical data concerning threshold is stored. For example, in the preferred embodiment using QT interval, critical data relating change of QT to threshold is stored. Alternately, for an embodiment of this invention utilizing QRS morphology, a critical change in the timing of the QRS may be stored. As indicated at block 123, the routine is initiated automatically, such as once a day. Following initiation of block 123, the pacemaker waits for the next cycle of 124. At 126, the pacemaker executes the programmed change of pulse output level, e.g., the voltage or the pulse width is decremented by a predetermined amount. As discussed in connection with the preferred QT embodiment, there may be a predetermined number of pulses delivered at each given output level. Following delivery of the pace pulse, as indicated at 128, the pacemaker obtains selected information from the evoked cardiac signal. For the QT embodiment, the pacemaker senses the T-wave, and determines the time interval between the delivered pacing pulse and a defined point of the QRS-T evoked response. Alternately, the width or slew rate of the evoked QRS or T-wave may be determined. Then, at 130, the determined information is compared with the stored critical data to see if there is an indication that the output level has dropped to a critical level. If no, the routine recycles to 124 and waits for the next cycle. However, if yes, this means that a measure of threshold has been determined, i.e., last output level was within a predetermined percentage of threshold. The routine then goes to block 132 and determines whether the output should be reset. If yes, output is reset at 134, and then the routine returns to block 123; if the output does not need to be reset, the routine goes straight to 123.

Before proceeding to a discussion of the preferred QT embodiment, it is noted generally that the invention provides a procedure for supplementing the normal method of determining pacing threshold in the ventricle. Normal measurements may be based on any available method, such as detection of the evoked response, either QRS or T-wave, or detection of the pump function, e.g., with a pressure sensor, impedance volume measurement, etc. As is known, during normal threshold measurement, the output energy is decreased until loss of capture. Although a more sophisticated device may include delivery of a powerful backup stimulus shortly after losing capture, this is not necessary. The normal threshold measurement may be performed during sleep or rest. Typically this is done at the time of visit to the patient's physician, under the control of an external programmer. In any event, in the practice of this invention, such normal threshold measurements are performed periodically. A benefit of this invention is that the time between such normal threshold measurement may be increased, since the invention provides a less intervening method to frequently estimate output margin versus threshold, which procedure does not require forcing loss of capture.

Figure 4A:
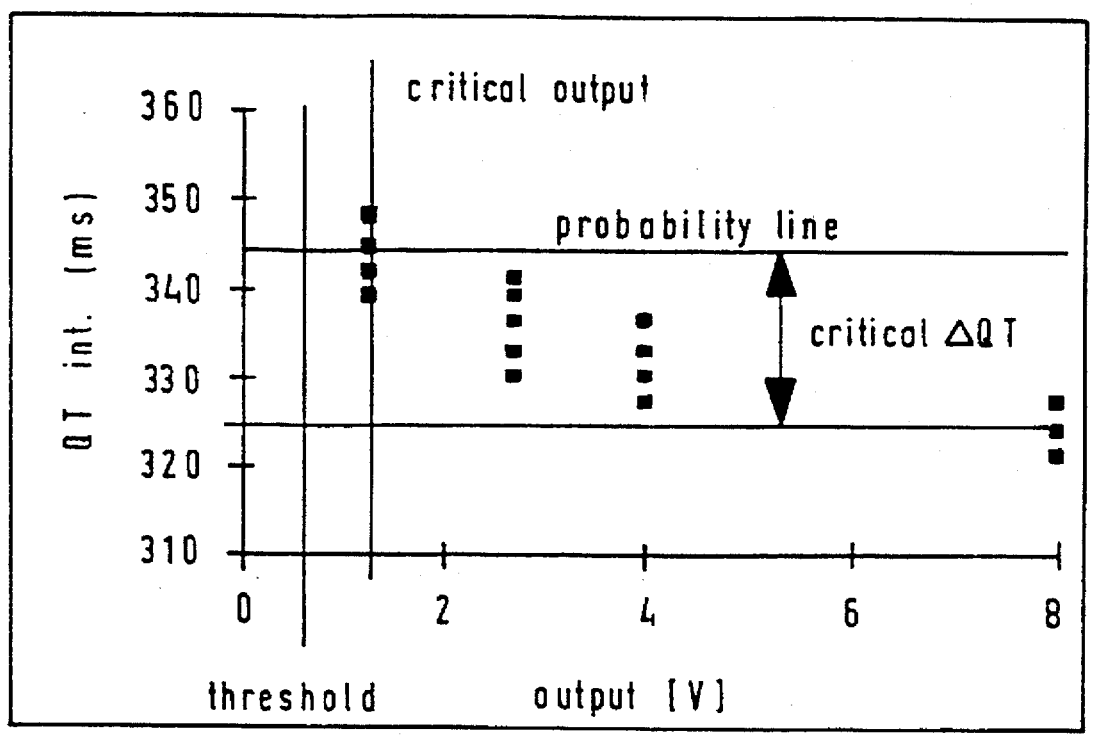
FIG. 4A is a graph showing the relation of QT interval as a function of pace pulse voltage output at a fixed rate, and indicating how a determination can be made when output is near threshold.

Referring now to FIG. 4A there is illustrated a plot of data, correlating QT interval (ms) with pace pulse output (volts) at a constant pacing rate. In the discussion that follows, it is to be understood that the correlation is substantially the same when considering variation of QT interval with output change in pulse width (ms). As seen, a set of data points is shown at each of a plurality of different output levels, i.e., 8 v; 4 v; 2.5 v; and 1.5 v. It is seen that in decreasing output from 8 v to 1.5 v, the QT interval increases from approximately 325 ms to about 345 ms. Also depicted in FIG. 4A is a vertical line, indicating the pace pulse voltage level corresponding to the threshold, i.e., below which the pace pulse would not result in capture. In practice, this is determined by actually dropping the voltage level in small increments until the threshold is determined. Also shown in FIG. 4A is a second vertical line at an output level not far above threshold, which is labelled "critical output", and two horizontal lines. Thus, seen in FIG. 4A, there is defined a value of "critical ΔQT", which is the increase in QT as output is dropped from 8 v to the critical value of about 1.5 v. The "probability line" illustrated at a QT of about 345 ms shows a value of QT for this patient at which there is a high probability that the pace pulse output level is near threshold, as determined from prior data obtained while the patient was at rest and being paced at a constant pacing rate, e.g., 70 bpm. The critical output is defined as that output where QT has risen to the probability line, indicating a high probability that the output is near threshold. Thus, the critical output is a measure of patient threshold.

Figure 4B:
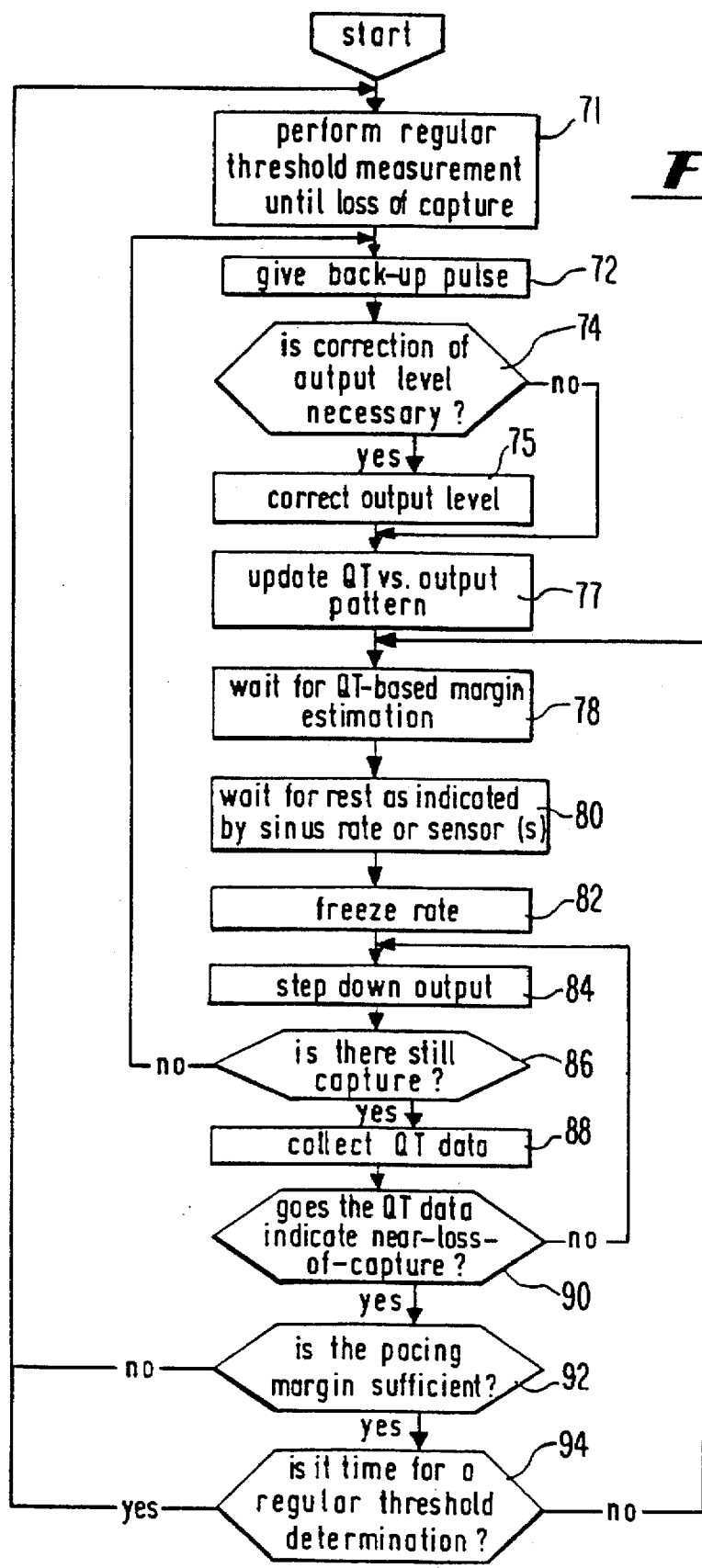
FIG. 4B is a flow diagram of the primary operations and logic for determining a measure of patient threshold in accordance with the preferred embodiment of this invention.

Referring to FIG. 4B, there are shown the primary steps of a routine carried out by the pacemaker, preferably built into the software, for determining a measure of threshold which supplements the regular threshold measurement. At the start of the routine, scattergram data as represented in FIG. 4A is stored in memory. This data may be obtained by a test at the time of implant, or may be updated data correlating variation of patient QT with pulse level. Importantly, the stored information contains data representative of actual patient threshold, as well as data showing the variation of QT as a function of changing pace pulse level, so that a "critical output" or equivalent measure of threshold is also determined and stored in the pacemaker. As illustrated at the beginning of the routine, the pacemaker performs a regular threshold measurement until loss of capture, as indicated at 71. This is preferably followed by delivery by a backup pulse, as indicated at 72, and as disclosed in the above-referenced U.S. Pat. No. 3,835,865. At 74, it is determined whether correction of the output level is necessary, i.e., does the presently programmed output level provide a sufficient safety margin? If correction is necessary, the routine goes to 75 and corrects the output level. If correction is not necessary, the routine branches directly to block 77, where the QT vs. output pattern is updated. In other words, at this step, if there has been a different threshold determined, this information is put into the stored data along with the latest QT-output scattergram data and, if necessary, new values of critical ΔQT and critical output are determined. For example, if threshold has increased, and critical output remains the same ΔV above threshold as previously set, the ΔQT is adjusted accordingly.

At 78, the routine waits for the expiration of a predetermined interval, e.g., 24 hours, 7 days, etc., or to initiate estimation of threshold margin based upon QT. When the pacemaker receives the signal to proceed, it carries out the function of block 80, namely it waits for the patient to be at rest. Rest can be determined by monitoring sinus rate or signals from one or more sensors, in a known manner. It is desirable to wait until the patient is in a stable rest condition so as to eliminate QT variations which would occur due to normal activity when not at rest. When rest has been indicated, the routine goes to 82 and freezes the rate at a predetermined level, e.g., 70, 80, or 90 bpm. Following this, the pacemaker steps down the output by a first increment. The increments can be programmed in any desired manner, and it is pointed out the increments illustrated in FIG. 4A are illustrative only. As long as capture occurs at a given output, a distributed sample of QT intervals will be measured at each output value. Thus, at each output level there may be N pulses delivered, and N detected QT intervals. Thus, the step corresponding to block 84 may involve delivering four or five successive pace pulses at the same voltage level. After each pace pulse, as indicated at 86, it is determined if there is still capture. If no, meaning that the output level has dropped below threshold, the routine loops back to 72 and provides a backup pulse. As long as there is still capture, QT data is collected and stored in memory, as indicated at 88. At 90, it is determined whether the QT data indicates near-lossof-capture, i.e., is QT at or above the probability line, such that there has been an increase in QT exceeding the critical ΔQT? If there is no such indication, the routine loops back to block 84, and continues with the output pace pulse being decremented by another increment. However, if a predetermined number of the N pulses have resulted in QT intervals above the probability line, this means that a measure of threshold has been found, i.e., the energy of the pace pulse has been reduced to the critical output which has been defined as being just a small margin above threshold. If at 92 the pacing margin is determined not to be sufficient, the routine loops back to block 71, and again proceeds through steps 71, 72, 74 and 75, to readjust the output level. However, if the pacing margin is found to be sufficient, the routine goes to block 94. There it is determined whether it is time for a regular threshold determination. Assuming no, the routine loops back to 78; if yes, it loops back to 71.

It is noted that as an alternative, at block 92, the pacemaker may also determine whether the output level (voltage or pulse duration) can be decreased and still maintain a sufficient margin. Thus, the pacemaker looks at the safety factor that is stored, and used at 75, and determines whether the present output level exceeds the safety margin such that output level can actually be decreased, saving battery expenditure. From the earlier normal threshold measurement, the pacemaker algorithm knows the ratio between the actual threshold and the output value which has now been associated with reaching the probability line. Adopting this ratio, the output margin can be re-estimated, providing a basis for adjusting the output level.

Although the preferred embodiment has been illustrated using the concept of determining a critical ΔQT, other techniques can be used to obtain a measure of actual threshold without causing loss of capture. For example, patient data may indicate that at the point where threshold is just reached due to a lowered output, the incremental increase in QT interval corresponding to decrease in output may have a slope value within a predetermined range. At any output level where this slope attains a predetermined percentage of threshold slope, e.g., 90% of the threshold slope, it can be concluded that this is an approximate measure of threshold. Thus, the invention obtains a measure of threshold which is a predetermined distance above threshold. This avoids loss of capture, but enables taking the test close to get an accurate measure of such actual threshold.

As discussed previously above, the invention can be carried out using other portions of the cardiac signal sensed by the lead. The morphology of the evoked QRS, or the morphology of the evoked T-wave, can be analyzed in a conventional manner, e.g., by measuring the width, peak value, surface area underneath the evoked signal, or slope of a portion of the wave. Similarly, for a pacemaker that is delivering only atrial pace pulses, e.g., an AAI pacemaker, the morphology of the evoked atrial contraction can be monitored and utilized to obtain a measure of threshold without undergoing loss of capture.

What is claimed:

1. An implantable cardiac pacemaker system, having a pacemaker and a lead for connecting signals between said pacemaker and a patient's heart, the pacemaker having a controllable pulse generator for generating and delivering pace pulses at a controlled output level, sensing means for sensing evoked cardiac signals from said patient representative of cardiac activity in response to delivered pace pulses, control means for controlling the output level of said generated and delivered pace pulses, and a battery for providing energy, further comprising:

program means for programming said control means to vary said pace pulse output level in accordance with a predetermined program;

information means for collecting information from each of said sensed cardiac signals during said predetermined program;

storage means for storing data relating to changes in said evoked signals as a function of pace pulse output level; and determining means for determining from said information and from said stored data a measure of patient threshold.

2. The pacemaker system as described in claim 1, wherein said storage means comprises a stored representation of prior actual patient threshold.

3. The pacemaker system as described in claim 2, wherein said storage system comprises stored data representative of prior determined values of QT and corresponding values of pace pulse output level.

4. The pacemaker system as described in claim 1, comprising means for updating said stored data.

5. The pacemaker system as described in claim 1, wherein said sensing means senses evoked T-waves, and said information means collects QT interval information.

6. The pacemaker system as described in claim 1, wherein said sensed signal information comprises data representative of evoked QRS wave morphology.

7. The pacemaker system as described in claim 1, wherein said sensed signal information comprises data representative of evoked T-wave morphology.

8. The pacemaker system as described in claim 1, wherein said sensed signals comprise T-waves, further comprising means for determining each QT interval corresponding to each said delivered pace pulse during said program, and said storage means comprises a stored value of a predetermined change in QT corresponding to a change from a predetermined high pace pulse output level to an output level near threshold.

9. The pacemaker system as described in claim 1, further comprising output adjust means for adjusting the output level of said pace pulses as a function of said threshold measure.

10. A pacemaker system for delivering pace pulses to a patient, said system having a pacemaker with a controllable pulse generator for generating pace pulses, control means for controlling the output level of said pace pulses, lead means for delivering pace pulses to the patient's heart and detecting patient heart signals, sensing means for sensing selected signals from the patient's heart, and energy source means for providing energy for said pacemaker, further comprising:

output program means for lowering the pace pulse output level in a predetermined manner, information means for obtaining information relating to each said sensed signal corresponding to a heartbeat evoked by a pace pulse of lowered level, and determining means for determining a measure of patient pacing threshold as a function of said information.

11. A pacemaker system as described in claim 10, wherein said information means comprises processing means for processing each said sensed signal in accordance with a first predetermined function to get processed data, and said determining means comprises means for determining said measure of patient threshold as a second function of said processed data.

12. The pacemaker system as described in claim 11, comprising storage means for storing information representative of the relation of said processed data to patient threshold.

13. The pacemaker system as described in claim 12, wherein said first function is QT interval, and wherein said storage means stores data representative of a critical change in QT interval corresponding to changed pace pulse output level.

14. A method for automatically obtaining a measure of patient threshold in an implantable pacemaker without dropping the output level of any delivered pace pulse below threshold, said pacemaker being powered by a battery and having a controllable pulse generator for generating and delivering pace pulses of controllable output level, comprising:

changing the output level of said pace pulses in accordance with a predetermined program;

sensing cardiac signals evoked by said pace pulses of changed output level and obtaining information from a predetermined portion of each said sensed signal; and determining when said information indicates that pace pulse output level has been changed to a level above but critically close to patient threshold, said determined critical level being a measure of patient threshold.

15. The method as described in claim 14, comprising adjusting said pace pulse output level as a function of said determined critical level.

16. The method as described in claim 14, wherein said sensing comprises sensing evoked T-waves, and said determining comprises determining the pulse level at which the time from a delivered pace pulse to an evoked T-wave corresponds to a value still above, but near threshold.

17. An implantable cardiac pacemaker system, having a pacemaker and a lead for connecting signals between said pacemaker and a patient's heart, the pacemaker having a controllable pulse generator for generating and delivering pace pulses at a controlled output level, sensing means for sensing evoked cardiac signals from said patient representative of cardiac activity in response to delivered pace pulses, control means for controlling the output level of said generated and delivered pace pulses, and a battery for providing energy, further comprising:

program means for programming said control means to vary said pace pulse output level in accordance with a predetermined program;

data means for collecting information relating to each Q-T interval following a pace pulse during said program, storage means for storing data representative of change in Q-T interval corresponding to change in pace pulse output level from a predetermined level to a level above but near threshold, and determining means for determining a measure of patient threshold as a function of said collected information and said stored data.

* * * * *